United States Patent
Ehrenreich et al.

(10) Patent No.: US 7,361,681 B2
(45) Date of Patent: Apr. 22, 2008

(54) METHOD OF TREATING AMYTROPHIC LATERAL SCLEROSIS USING MELATONIN

(75) Inventors: Hannelore Ehrenreich, Goettingen (DE); Ruediger Hardeland, Goettingen (DE); Klaus-Armin Nave, Goettingen (DE); Jochen Weishaupt, Goettingen (DE)

(73) Assignee: SYGNIS Bioscience GmbH & Co. KG, Heidelberg (DE)

( * ) Notice: Subject to any disclaimer, the term of this patent is extended or adjusted under 35 U.S.C. 154(b) by 504 days.

(21) Appl. No.: 10/400,697

(22) Filed: Mar. 28, 2003

(65) Prior Publication Data

US 2004/0192745 A1  Sep. 30, 2004

(51) Int. Cl.
*A61K 31/405* (2006.01)
*A61K 31/40* (2006.01)
*A61K 31/425* (2006.01)

(52) U.S. Cl. .............. 514/415; 514/419; 514/367

(58) Field of Classification Search ............... 514/415, 514/419
See application file for complete search history.

(56) References Cited

U.S. PATENT DOCUMENTS

| 3,642,994 | A | * | 2/1972 | Fernando ............... 514/419 |
| 5,591,768 | A | * | 1/1997 | Lewy et al. ............ 514/415 |
| 5,700,828 | A | | 12/1997 | Federowicz et al. |
| 5,780,489 | A | * | 7/1998 | Brooks ................. 514/369 |
| 6,004,991 | A | * | 12/1999 | Fourtillan et al. ...... 514/415 |
| 6,274,615 | B1 | * | 8/2001 | Pappolla et al. ........ 514/415 |
| 6,353,015 | B1 | | 3/2002 | Oxenkrug et al. |
| 6,436,984 | B1 | | 8/2002 | Ducrocq et al. |
| 6,458,384 | B2 | | 10/2002 | Jaenicke et al. |
| 6,469,049 | B1 | | 10/2002 | Meyerhoff et al. |

OTHER PUBLICATIONS

Bowling et al. Bioenergetic and oxidative stress in neurodegenerative diseases. Life Sciences, 1995, vol. 56, No. 14, pp. 1151-1171.*
J. Pineal Research, 2002; 33:186-187, Melatonin as a candidate compound for neuroprotection in amyotrophic lateral sclerosis (ALS): high tolerability of daily oral melatonin administration in ALIS patients.
Iacovitti, et al. Brain Research, 768 (1997) 317-326, Melatonin rescues dopamine neurons from cell death in tissue culture models of oxidative stress.
Cazevieille, et al., Brain Research, 768 (1997) 12-24, Melatonin protects primary cultures of rat cortical neurons from NMDA excitotoxicity and hypoxial/reoxygenation.
General Anti Oxidant Information, Feb. 1998, www.home.goulbum.net.au/shack/antioxidants.htm.

* cited by examiner

*Primary Examiner*—Jennifer Kim
(74) *Attorney, Agent, or Firm*—Oblon, Spivak, McClelland, Maier & Neustadt, P.C.

(57) ABSTRACT

The present invention relates to the treatment of amyotrophic lateral sclerosis (ALS) and/or the improvement of motor function in individuals in need of such improvement using a melatonin compound or a pharmaceutical salt of the melatonin compound.

25 Claims, 2 Drawing Sheets

METHOD OF TREATING AMYTROPHIC LATERAL SCLEROSIS USING MELATONIN

BACKGROUND OF THE INVENTION

1. Field of the Invention

The present invention relates to the treatment of amyotrophic lateral sclerosis (ALS), the improvement of motor function and/or the prevention of a loss thereof in individuals in need of such improvement/prevention.

2. Description of the Background

Amyotrophic lateral sclerosis (ALS) is a fatal motor neuron disease, affecting both the first and second motoneuron. The progression of ALS is characterized by a degeneration of motor neurons associated with a dramatic demyelination in the anterior horn of the spinal cord. The etiology is only partially understood. Of the 5-10% familial cases, 20% carry a mutation of the superoxide dismutase 1 (SODI) gene. Such a mutation is also present in 5% of the sporadic cases (Rowland *New Engl J Med* 2001:344:1688-1700).

Pathophysiologically, three major mechanisms are discussed in ALS: (a) mutations of the SODI gene, causing a toxic gain of function with enhanced reactivity towards abnormal substrates (tyrosine nitration), along with an impaired ability to bind zinc leading to a reduced antioxidant capacity; (b) mutations in neurofilament genes and oxidative modifications or hyperphosphorylation of cytoskeletal proteins leading to selective motor axon degeneration; (c) excitotoxicity caused by increased cerebrospinal fluid glutamate levels together with a loss of excitatory amino acid transporters (Rowland *New Engl J Med* 2001:344:1688-1700).

There is no promising treatment available to date. The only compound yielding borderline significance with respect to survival time is RILUZOLE® (2-amino-6-(trifluoromethoxy) benzothiazole), an antiexcitotoxin (Rowland *New Engl J Med* 2001:344:1688-1700). As the common basis of cellular and extracellular alterations in ALS seems to be oxidative stress mediated by reactive nitrogen/oxygen species, future attempts of treatment might focus on antioxidant strategies involving suppression of nitric oxide (NO) synthase.

Accordingly, there remains a prominent need for new therapies for improving or preventing the loss of motor function in such patients, such as ALS patients.

Melatonin and melatonin derivatives are known to obey and affect circadian rhythms in mammals when secreted from the pineal gland during the night (Reiter *Prog Clin Biol Res* 1981: 59C: 223-233; Stokkan & Reiter *J Pineal Res* 1994: 16: 33-36; Petrie et al., BMJ 1989: 298: 705-707). Based on these observations, melatonin is often used off the shelf for treating jet lag.

Melatonin is also well-known as an antioxidant in neuronal and non-neuronal tissues (*J. Pineal Res*. 1994: 17:94-100 and *Life Sci* 1994: 56:83-89). In fact, such antioxidant properties have been shown to rescue dopamine neurons from damage in an experimental model system (Iacovitti et al *Brain Res* 1997: Sep. 12: 768(1-2): 317-26, Melatonin rescues dopamine neurons from cell death in tissue culture models of oxidative stress). In addition, melatonin (at doses of 100 μM) has been shown to "counteract the in vitro destructive effects of NMDA or hypoxia/reperfusion by preventing accumulation of excessive free radicals" (Cazeville et al *Brain Res* 1997:768(1-2): 120-124). From these observations of the antioxidant properties of melatonin have been prescribed at 3 mg melatonin doses in the evening to ALSIMNI patients (Dr. Stanley Appel of the Baylor Clinic in Texas).

Melatonin and various melatonin derivatives have been described as being useful for treating anoxic or ischemic brain injury (U.S. Pat. No. 5,700,828).

However, melatonin has not been assessed for its effects when administered episodically at night in high doses in ALS patients or in patients with other related neurodegenerative disorders.

SUMMARY OF THE INVENTION

Accordingly, it is an object of the present invention to provide a new method for treating ALS patients by using melatonin and melatonin derivatives.

It is also another object of the present invention to improve motor function in patients in need thereof, for example, ALS patients by using melatonin and melatonin derivatives.

It is another object of the present invention to provide a prophylactic treatment to individuals at risk of developing ALS or related motor neuron diseases.

A more complete appreciation of the invention and many of the attendant advantages thereof will be readily obtained as the same becomes better understood by reference to the following detailed description when considered in connection with the accompanying drawings, wherein:

DETAILED DESCRIPTION OF INVENTION

Figure 1:
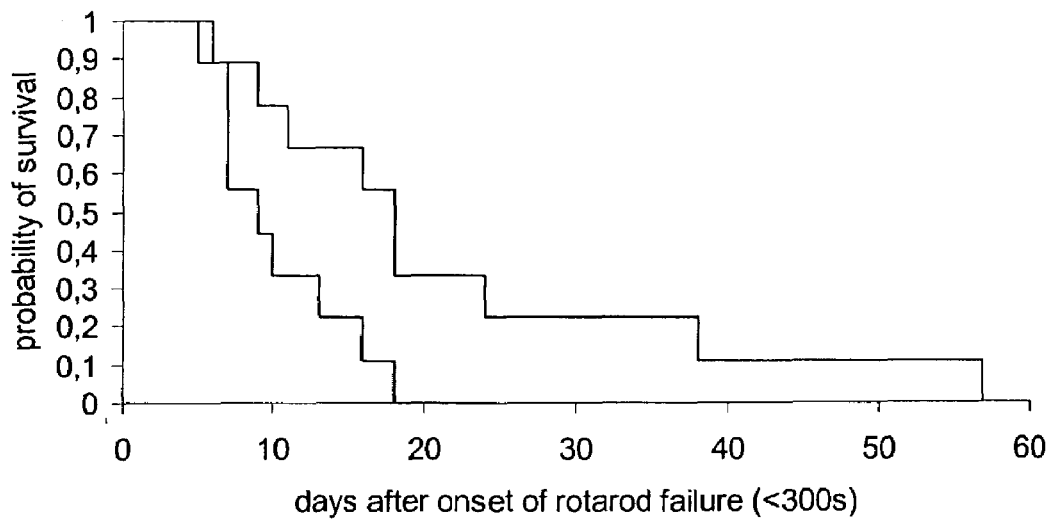
FIG. 1 is a depiction of rotorod test data obtained from melatonin versus vehicle (solvent only) treated SODG93A mice (n=9-12 per group). Rotarod failure is defined to start when mice are no longer able to stay in the rotarod for more than 300 sec (=early disease state). The days from that time point to death are significantly more in melatonin than in vehicle treated mice.
Figure 2:
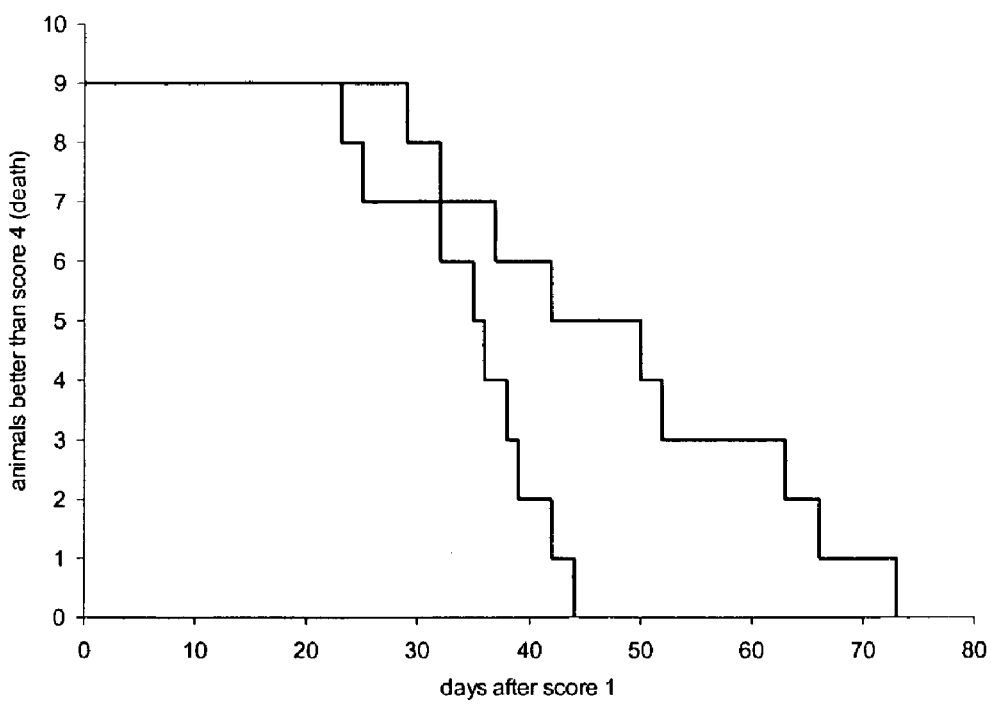
FIG. 2 is a depiction of clinical score data obtained from melatonin versus vehicle (solvent only) treated SODG93A mice (n=9-12 per group). Shown are days after score 1 (abnormal hindlimb reflex or tremor in at least one extremity or asymmetrical gait) to score 4 (endpoint criteria/death). The days from score 1 to death are significantly more in melatonin than in vehicle treated mice.

Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Patients who would benefit from the administration of melatonin include ALS patients and patients with related motor neuron disease.

Since melatonin appears to be free from side effects even upon long-term applications, melatonin can be used as a prophylaxis to treat those patients that are at risk of developing ALS. Such patients would be those that have been identified with the genetic marker associated with ALS, i.e., familial form of ALS, and those patients who exhibit early signs of motor neuron disease, such as impaired motor control.

The treatment of those patients who would benefit from improved motor function are those with motor function loss that is a result of a particular neurodegenerative disease, such as amyotrophic lateral sclerosis and other peripheral neuropathies.

The treatment protocol can also include administering to the patients one or more additional agents that could improve motor function or improve the overall disease outlook of the patient. For example, RILUZOLE® (2-amino-6-(trifluoromethoxy)benzothiazole), erythropoietin compounds (inclusive of erythropoietin analogues/derivatives such as those described in U.S. Pat. Nos. 6,340,742, 5,547,933, 5,888,772, and 5,856,298), magnesium, selen, creatine, amino acids, vitamins (for example, vitamin A, C, D, and E), cannabinoids, estrogens, androgens, endothelins, orexins, GDNF, thrombopoietin and other growth factors such as GM-CSF, G-CSF, and N-acetylserotonin and pinoline (6-methoxy-1,2,3,4-tetrahydro beta-carboline) (Reiter et al *Adv Exp Med Biol* 1999: 167: 379-387).

By "treating" is meant the slowing, interrupting, arresting or stopping of the progression of the disease or condition and does not necessarily require the complete elimination of all disease symptoms and signs. "Preventing" is intended to include the prophylaxis of the neurological disease, wherein "prophylaxis" is understood to be any degree of inhibition of the time of onset or severity of signs or symptoms of the disease or condition, including, but not limited to, the complete prevention of the disease or condition.

"Improving," "Improvement," or "Improved" as it relates to motor function is meant to mean any appreciable increase in motor function as measured using standard methodology known in the field.

Melatonin is a hormone, N-acetyl-5-methoxytryptamine, that is produced by the pineal gland particularly during the evening because its' secretion is stimulated by the dark and inhibited by light. Melatonin is produced in a pathway where tryptophan in the pineal gland is converted to serotonin and ultimately melatonin (see also Bernard et al *Reprod Nutr Dev* 1999 May-Jun: 39(3):325-34). Melatonin has been reported to have direct effects on circadian rhythms (Weaver et al. *J Clin Endocrinol Metab* 1993: February 76(2):295-301).

Melatonin, in clinical use for many years, is well tolerated and safe. Applications include altered day-night-cycle induced by shift work or jet lag, sleep induction and immune enhancement (Tan et al *Curr Top Med Chem* 2002: 2:181-197; Seabra et al *J Pineal Res*. 2000: 29:193-200). At present, melatonin is being tested in clinical trials for treatment of Alzheimer disease because of its capacity to reduce in vitro Aβ formation as well as aggregation and neurotoxicity (Reiter *Prg. Neurobiol* 1998; 56:359-384). The doses applied range from 1 to 2000 mg (short term) per day in cancer studies. Applications in humans are predominantly oral (Seabra et al *J Pineal Res*. 2000: 29:193-200).

Melatonin has a unique broad spectrum of effects including scavenging of hydroxyl, carbonate, alkoxyl, peroxyl and aryl cation radicals, stimulation of glutathione peroxidase and other protective enzymes, but also suppression of NO synthase. The interference with NO metabolism has multiple consequences: down-regulation of NO formation counteracts damage by peroxynitrite-dependent radicals as well as $Ca^{2+}$-dependent excitotoxicity. This pleiotropy may explain, at least in part, why melatonin has been identified as a potent neuroprotectant, e.g., by attenuating oxidative damage after experimental neurotrauma (Reiter *Prg Neurobiol* 1998: 56:359-384; Tan et al *Curr Top Med Chem* 2002: 2:181-197).

In addition, melatonin, because of its amphiphilicity, readily crosses the blood-brain barrier (*J. Pineal Res.* 1988: 5:437-453). Although melatonin seems to have a rapid turnover, the administration of slow release preparations maintains high plasma levels for about 6 hr.

In addition to melatonin, melatonin derivatives and melatonin analogues are known in the art and may be employed in place of or in combination with melatonin itself (see U.S. Pat. No. 6,436,984; Faust et al *J Med. Chem*. 2000: 43(6): 1050-1061; Gozzo et al *Free Radic. Biol. Med*. 1999: 26 (11-12):1538-1543; Hu et al *Melanoma Res*. 1998 8(3):205-210; Methe-Allainmat et al 1996: 39(16):3089-3095; Garratt et al *J Med. Chem*. 1996: 39(9):1797-1805). Collectively, melatonin, melatonin derivatives and melatonin analogues are termed melatonin compounds herein.

Melatonin may be administered as a pharmaceutically acceptable salt, which include, but are not limited to, addition salts with inorganic acids or with organic acids. Compositions of melatonin used in the invention may comprise, for example, at least one melatonin compound in its free form, its pharmaceutically acceptable salt form, or combinations of these.

A therapeutically effective amount of melatonin or dosage for treating neurodegenerative diseases, such as ALS and peripheral neuropathies is an amount that results in at least an improved motor function and, preferably, an appreciable improvement in the overall health of the patient. For the purposes of the present invention such an amount is from about 30 to 600 mg of melatonin, inclusive of 30 to 60 mg and 300 to 600 mg which would relate to about 0.5 to about 10 mg/kg body weight and can be altered based on age, race, sex, and other factors based on the individual patient.

Melatonin can be formulated according to the mode of administration and combined with one or more various pharmaceutically acceptable carriers and/or excipients. The term "pharmaceutically acceptable" refers to molecules and compositions that are physiologically tolerable and do not typically produce an allergic or similar unwanted reaction such as gastric upset or dizziness when administered. "Pharmaceutically acceptable" means approved by a regulatory agency of the Federal or a state government or listed in the U.S. Pharmacopoeia or other generally recognized pharmacopoeia for use in animals, preferably humans. The term "carrier" refers to a diluent, adjuvant, excipient, or vehicle with which the compound is administered. Such pharmaceutical carriers can be sterile liquids, such as saline solutions, dextrose solutions, glycerol solutions, water, and oils emulsions such as those made with oils of petroleum, animal, vegetable, or synthetic origin (peanut oil, soybean oil, mineral oil, or sesame oil). Water, saline solutions, dextrose solutions, and glycerol solutions are preferably employed as carriers, particularly for injectable solutions.

When melatonin is administered in a combination, it may be premixed with additional compounds prior to administration, administered simultaneously, or administered in series. The route of administration can include the typical routes including, for example, orally, subcutaneously, transdermally, rectally, intravenously, intraarterially, by direct injection to the brain, and parenterally. Since patients suffering from ALS have a loss of motor function, which includes a difficulty in swallowing, a preferred mode of administration is rectally using, for example, an enema, a suppository, and other similar delivery vehicles.

In one aspect of the present invention, melatonin is administered to the patients at night, e.g. just before the patient goes to sleep, to imitate an episodic release pattern with intervals aiming at maintenance of the melatonin biorhythm. Based on this administration it may be possible to prevent alterations in antioxidative enzyme systems and/or development of tolerance, i.e. loss of efficiency.

An exemplary administration is a suppository formulated to contain not less than 300 mg of melatonin or a melatonin derivative, which is administered at night.

EXAMPLES

Example 1

Three ALS patients with an estimated onset of disease 2-4 yr previously, were included in a pilot program in Göttingen, set up to explore potential effects and side-effects of chronic high-dose melatonin in this condition. Intraindividual follow-up (upon entering the study, and after 1, 2, 6, 9 and 13 months of treatment thus far) included physical examination/clinical rating scales (ALS functional rating scale, ALSFRS), pulmonary function test, EMG-NCV, routine laboratory parameters, psychological rating scales, as well as magnetic resonance imaging and MR spectroscopy. Patients received 30-60 mg of melatonin as an oral slow release formulation in the late evening. In addition, they continued their "regular medication" in the morning and at noon (RIUZOLE® 50-100 mg, vitamins C and E, creatine, amitriptylin).

Melatonin was well tolerated over the entire observation period. No side effects have been reported or detected thus far. In particular, no signs of fatigue have been noted. The only problem identified to date is that ALS patients, compromised in their swallowing function, have to swallow 10-20 melatonin tablets (slow release formulations of melatonin is available only in 3 mg tablets).

The clinical rating scales (ALSFRS) of the three patients from the start of the trial to one year later were: 34 to 22; 25 to 11; 31 to 20, respectively. Whereas the patient with the most advanced state of ALS showed a progressive score decrease, two patients displayed an essentially stable score over time with an abrupt score drop at the last examination. Regarding the vital capacity of the lung, there was a distinctly reduced function (to less than 90%) already at the onset of this pilot study or in the early follow-up, respectively, indicating rather advanced stages of the disease upon inclusion of the patients. Clinical laboratory parameters including complete blood cell count, sodium, potassium, calcium, magnesium, chloride, total protein, blood glucose levels, triglycerides, total cholesterol, urea, creatinine, glutamic-oxalacetic transaminase, glutamic-pyruvate transaminase, GGT, GLDH, bilirubin, alkaline phosphatase, iron and c-reactive protein, did not show alterations during melatonin treatment.

To conclude, this is the first study reporting on the chronic application of high-dose melatonin over more than 1 yr. It is not possible to draw definitive conclusions on the efficacy of melatonin in the treatment of ALS based on the present data. The high tolerability of daily oral melatonin in ALS patients, however, may encourage the use of this compound in a double-blind proof-of-concept trial.

Example 2

Using SODG93A-transgenic mice as an animal model for ALS, we were able to show significant improvement in survival and course of disease, including several functional and behavioral parameters, e.g. rotarod performance, progression of paresis or weight loss, upon high oral melatonin treatment. No adverse effects of systemic melatonin were observed, even after application of several months. Melatonin was continuously applied via drinking water (0.5 mg/ml of water containing 1% of ethanol to enable a saturated solution of melatonin) starting on day 28 of life and continued until death. The vehicle control received water containing 1% of ethanol.

Obviously, numerous modifications and variations of the present invention are possible in light of the above teachings. It is therefore to be understood that within the scope of the appended claims, the invention may be practiced otherwise than as specifically described herein.

The invention claimed is:

1. A method for the treatment of a patient suffering from amyotrophic lateral sclerosis, comprising administering melatonin or a pharmaceutical salt thereof in an amount of at least 300 mg to the patient.

2. The method of claim 1, wherein said administering comprises rectal administration.

3. The method of claim 2, wherein said rectal administration comprises administering a suppository.

4. The method of claim 1, wherein the amount is from 300 to 600 mg.

5. The method of claim 1, wherein the melatonin is N-acetyl-5-methoxytryptamine or a pharmaceutically acceptable salt thereof.

6. The method of claim 5, which further comprises administering 2-amino-6-(trifluoromethoxy) benzothiazole.

7. The method of claim 5, wherein the N-acetyl-5-methoxytryptamine or a pharmaceutically acceptable salt thereof is administered rectally with a suppository.

8. The method of claim 1, which further comprises administering at least one compound selected from the group consisting of 2-amino-6-(trifluoromethoxy)benzothiazole, erythropoietin, magnesium, selen, creatine, an amino acid, a vitamin, a cannabinoid, an estrogen, an androgen, endothelin, orexin, GDNF, thrombopoietin, GM-CSF, G-CSF, N-acetylserotonin, and 6-methoxy-1,2,3,4-tetrahydro beta-carboline.

9. The method of claim 8, wherein the compound is a vitamin.

10. The method of claim 9, wherein the vitamin is at least one of vitamin A, vitamin C, vitamin D, and vitamin E.

11. The method of claim 1, wherein the administrating comprises a suppository with at least 300 mg of the melatonin.

12. A method of improving motor function in a patient suffering from amyotrophic lateral sclerosis and impaired motor function, comprising administering melatonin or a pharmaceutical salt thereof in an amount of at least 300 mg to the patient to improve the motor function of the patient relative to the motor function of the patient before the administering.

13. The method of claim 12, wherein said administering comprises rectal administration.

14. The method of claim 13, wherein said rectal administration comprises administering a suppository.

15. The method of claim 12, wherein the amount is from 300 to 600 mg.

16. The method of claim 12, wherein the melatonin is N-acetyl-5-methoxytryptamine or a pharmaceutically acceptable salt thereof.

17. The method of claim 16, which further comprises administering 2-amino-6-(trifluoromethoxy) benzothiazole.

18. The method of claim 16, wherein the N-acetyl-5-methoxytryptamine or a pharmaceutically acceptable salt thereof is administered rectally with a suppository.

19. The method of claim 12, which further comprises administering at least one compound selected from the group consisting of 2-amino-6-(trifluoromethoxy)benzothiazole, erythropoietin, magnesium, selen, creatine, an amino acid, a vitamin, a cannabinoid, an estrogen, an androgen, endothelin, orexin, GDNF, thrombopoietin, a GM-CSF compound, G-CSF, N-acetylserotonin, and 6-methoxy-1,2,3,4-tetrahydro beta-carboline.

20. The method of claim 19, wherein the compound is a vitamin.

21. The method of claim 20, wherein the vitamin is at least one of vitamin A, vitamin C, vitamin D, and vitamin E.

22. The method of claim 12, wherein the administrating comprises a suppository with at least 300 mg of the melatonin.

23. The method of claim 1, wherein the administering is for at least one year.

24. The method of claim 12, wherein the administering is for at least one year.

25. The method of claim 1, wherein the administering is at night.

\* \* \* \* \*